United States Patent [19]
Yuda et al.

[11] Patent Number: 6,117,818
[45] Date of Patent: *Sep. 12, 2000

[54] COMPOSITION FOR REGULATING PLANT GROWTH AND A METHOD FOR APPLICATION THEREOF

[75] Inventors: Atsuhiko Yuda, Kawachinagano; Tsutomu Mabuchi, Osakasayama; Hatsue Matsuura; Yoichi Hachitani, both of Kawachinagano, all of Japan

[73] Assignee: Nihon Nohyaku Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/693,967

[22] Filed: Aug. 7, 1996

[30] Foreign Application Priority Data

Aug. 12, 1995 [JP] Japan .................. 7-227418

[51] Int. Cl.$^7$ .................................. A01N 43/56
[52] U.S. Cl. ..................... 504/169; 504/280; 504/282
[58] Field of Search ................... 504/280, 282, 504/169; 548/366.1, 370.1, 370.4, 375.1, 376.1, 377.1

[56] References Cited

U.S. PATENT DOCUMENTS

| | | | |
|---|---|---|---|
| 5,032,165 | 7/1991 | Miura et al. | 71/92 |
| 5,112,384 | 5/1992 | Miura et al. | 71/92 |

FOREIGN PATENT DOCUMENTS

| | | | |
|---|---|---|---|
| 0 447 055 | 9/1991 | European Pat. Off. | C07D 231/22 |
| 3-163063 | 7/1991 | Japan . | |
| 4-211065 | 8/1992 | Japan . | |
| 2 274 780 | 8/1994 | United Kingdom | A01N 25/30 |

OTHER PUBLICATIONS

Hopkins, William L. *Global Herbicide Directory.* 1st ed. Ag Chem Information Services: Indianapolis, IN. P. 92. 1994.
Hungarian Search Report dated Aug. 8, 1997, issued in a counterpart foreign application.
CA Abstract 121:274460A, 1994.
CA Abstract 117:42744K, 1992.
CA Abstract 116:101131N, 1991.

*Primary Examiner*—S. Mark Clardy
*Attorney, Agent, or Firm*—Pillsbury Madison & Sutro

[57] ABSTRACT

A composition for regulating plant growth which comprises as an active ingredient(s) at least one 3-substituted phenylpyrazole derivative represented by the general formula (I):

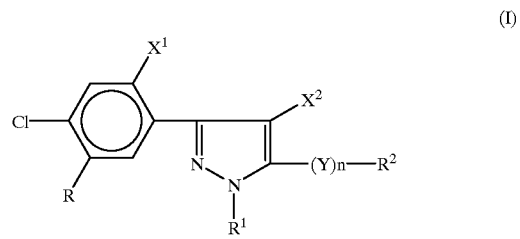

and acts as a desiccant or defoliant for root vegetables (e.g. potato), fiber crops (e.g. cotton), oil crops (e.g. soybean and sunflower) and cereals (e.g. rice); and a method for applying said composition.

10 Claims, No Drawings

COMPOSITION FOR REGULATING PLANT GROWTH AND A METHOD FOR APPLICATION THEREOF

BACKGROUND OF THE INVENTION

1. Field of the Invention

The present invention relates to a composition for regulating plant growth and a method for applying the same.

2. Related Art

The 3-substituted phenylpyrazole derivative represented by the general formula (I) shown hereinafter which is used in the present invention is a compound described in Japanese Patent Unexamined Publication Nos. 3-163063 and 4-211065. As a foliage applied herbicide, said derivative has an excellent herbicidal activity against all of herbaceous weeds which are harmful to upland farming. Particularly when applied for wheat (barley, oats or rye) cropping, said derivative exhibits a marked herbicidal effect on typical weeds such as cleavers (*Galium aparine*), chickweed (*Stellaria media*), birdseye speedwell (*Veronica persica*), sentless chamomile (*Matricaria inodora*), purple deadnettle (*Lamium purpureum*), henbit (*Lamium amplexicaule*), shepherd's purse (*Capsella bursa-postoris*), marsh yellowcress (*Rorippa islandica*), sticky chickweed (*Cerastium viscosum*), common lambsquarters (*Chenopodium album*), tufted knotweed (*Polygomum longisetum*), prostrate knotweed (*Polygonum aviculare*), etc.

SUMMARY OF THE INVENTION

There is desired the development of a novel plant growth regulator (e.g. desiccant or defoliant) used for facilitating harvesting of root vegetables (e.g. potato), fiber crops (e.g. cotton), oil crops (e.g. soybean and sunflower) and cereals (e.g. rice). The present inventors earnestly investigated for developing a novel composition for regulating plant growth, and consequently found that a 3-substituted pyrazole derivative, a compound well known as a herbicide is useful for preparing a composition for regulating plant growth, such as a desiccant or defoliant for root vegetables (e.g. potato), fiber crops (e.g. cotton), oil crops (e.g. soybean and sunflower) and cereals (e.g. rice), whereby the present invention has been accomplished.

DETAILED DESCRIPTION OF PREFERRED EMBODIMENTS

The composition for regulating plant growth of the present invention is characterized by containing as an active ingredient(s) at least one 3-substituted pyrazole derivative represented by the general formula (I):

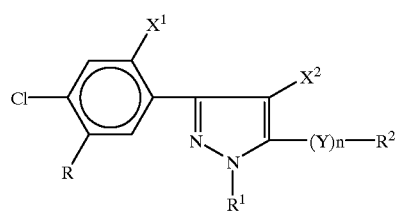

(I)

wherein R is $$-Y^1R^3$$

(wherein $R^3$ is a $(C_{1-6})$alkyl group, a halo$(C_{1-6})$alkyl group, a $(C_{2-6})$alkenyl group or a $(C_{2-6})$alkynyl group, and $Y^1$ is —O— or —S—), $$-Y^2CH(R^4)CO-OR^5$$

(wherein $R^4$ is a hydrogen atom or a $(C_{1-6})$alkyl group, $R^5$ is a hydrogen atom, a $(C_{1-6})$alkyl group, a halo-$(C_{1-6})$alkyl group, a $(C_{2-6})$alkenyl group or a $(C_{2-6})$-alkynyl group, and $y^2$ is —O—, —S— or —NH—), $$-COOCH(R^4)CO-Y^1R^5$$

(wherein $R^4$, $R^5$ and $Y^1$ are as defined above), or $$-COOR^6$$

(wherein $R^6$ is a $(C_{1-6})$alkyl group, a halo$(C_{1-6})$alkyl group, a $(C_{2-6})$alkenyl group or a $(C_{2-6})$alkynyl group), $R^1$ is a $(C_{1-6})$alkyl group, $R^2$ is a hydrogen atom, a $(C_{1-6})$alkyl group or a halo$(C_{1-6})$alkyl group, $X^1$ and $X^2$, which may be the same or different, are halogen atoms, Y is —O—, —S—, —SO—, —SO— or —NH—, and n is an integer of 0 or 1. The present invention relates also to a method for applying said composition for regulating plant growth.

In the definition of the substituents of the 3-substituted pyrazole derivative of the general formula (I), the term "$(C_{1-6})$alkyl group" means a linear or branched alkyl group of 1 to 6 carbon atoms, such as methyl, ethyl, n-propyl, i-propyl, n-butyl, i-butyl, s-butyl, t-butyl, n-pentyl, n-hexyl or the like. The prefix "halo" is used for expressing that a group contains one or more halogen atoms selected from chlorine, fluorine, bromine and iodine atoms. The term "halo$(C_{1-6})$alkyl group" means a substituted and linear or branched alkyl group of 1 to 6 carbon atoms having as the substituent(s) one or more halogen atoms which may be the same or different and are selected from the group consisting of chlorine atom, fluorine atom, bromine atom and iodine atom. The terms "$(C_{2-6})$alkenyl group" and "$(C_{2-6})$alkynyl group" mean linear or branched alkenyl and alkynyl, respectively, groups of 2 to 6 carbon atoms.

Typical compounds as the 3-substituted phenyl-pyrazole derivative(s) of the general formula (I), i.e., the active ingredient(s) used in the present invention are listed in Table 1 but they are not intended in any way to limit the scope of the present invention.

General Formula (I)

TABLE 1

[Structure diagram: 4-chloro-2-X¹-phenyl substituted pyrazole with R at phenyl, R¹ on N, X² at pyrazole 4-position, and (Y)n—R² at pyrazole 5-position] (I)

| | R | R² | X¹ | X² | (Y)n | Physical property |
|---|---|---|---|---|---|---|
| 1 | OCH₂CH=CH₂ | CH₃ | Cl | Cl | S | nD 1.6131 (25.3° C.) |
| 2 | OCH₂CH=CH₂ | CHF₂ | Cl | Cl | O | nD 1.5536 (28.4° C.) |
| 3 | OCH₂CH=CH₂ | CHF₂ | F | Cl | O | m.p. 63.7–64.1° C. |
| 4 | SCH₂CH=CH₂ | CH₃ | Cl | Cl | S | paste |
| 5 | SCH₂CH=CH₂ | CHF₂ | Cl | Cl | O | m.p. 52.0–55.0° C. |
| 6 | SCH₂CH=CH₂ | CHF₂ | F | Cl | O | nD 1.5670 (17.9° C.) |
| 7 | OCH₂C≡CH | CH₃ | Cl | Cl | S | m.p. 71.5° C. |
| 8 | OCH₂C≡CH | CHF₂ | Cl | Cl | O | m.p. 84.0° C. |
| 9 | OCH₂C≡CH | CHF₂ | F | Cl | O | m.p. 98.0–98.1° C. |
| 10 | SCH₂C≡CH | CH₃ | Cl | Cl | S | m.p. 94.5° C. |
| 11 | SCH₂C≡CH | CHF₂ | Cl | Cl | O | m.p. 127–129° C. |
| 12 | SCH₂C≡CH | CHF₂ | F | Cl | O | m.p. 82.8° C. |
| 13 | OCH₂COOCH₃ | CH₃ | Cl | Cl | S | m.p. 126.2° C. |
| 14 | OCH₂COOCH₃ | CHF₂ | Cl | Cl | O | m.p. 119.8° C. |
| 15 | OCH₂COOCH₃ | CHF₂ | Cl | Br | O | m.p. 133.8° C. |
| 16 | OCH₂COOCH₃ | CHF₂ | F | Cl | O | m.p. 122.8–123.1° C. |
| 17 | OCH₂COOC₂H₅ | CH₃ | Cl | Cl | S | m.p. 106.5° C. |
| 18 | OCH₂COOC₂H₅ | CHF₂ | Cl | Cl | O | m.p. 102.3° C. |
| 19 | OCH₂COOC₂H₅ | CHF₂ | F | Cl | O | m.p. 127.6° C. |
| 20 | OCH₂COOC₃H₇-n | CHF₂ | Cl | Cl | O | m.p. 89.7° C. |
| 21 | OCH₂COOC₃H₇-n | CHF₂ | F | Cl | O | m.p. 97.6–97.8° C. |
| 22 | OCH₂COOC₃H₇-i | CHF₂ | Cl | Cl | O | m.p. 106.0° C. |
| 23 | OCH₂COOC₃H₇-i | CHF₂ | F | Cl | O | m.p. 120.3–120.5° C. |
| 24 | OCH₂COOCH₂CH=CH₂ | CHF₂ | Cl | Cl | O | m.p. 84.7° C. |
| 25 | OCH₂COOCH₂CH=CH₂ | CHF₂ | F | Cl | O | m.p. 89.2–89.4° C. |
| 26 | OCH₂COOCH₂C≡CH | CHF₂ | Cl | Cl | O | m.p. 119.6° C. |
| 27 | OCH₂COOCH₂C≡CH | CHF₂ | F | Cl | O | m.p. 99.0° C. |
| 28 | OCH(CH₃)COOH | CH₃ | Cl | Cl | S | m.p. 191–194° C. |
| 29 | OCH(CH₃)COOCH₃ | CH₃ | Cl | Cl | S | m.p. 90–93° C. |
| 30 | OCH(CH₃)COOCH₃ | CHF₂ | F | Cl | O | m.p. 95.6° C. |
| 31 | OCH(CH₃)COOC₂H₅ | CH₃ | Cl | Cl | S | nD 1.5763 (28.8° C.) |
| 32 | OCH(CH₃)COOC₂H₅ | CHF₂ | Cl | Cl | O | nD 1.5238 (25.7° C.) |
| 33 | OCH(CH₃)COOC₂H₅ | CHF₂ | Cl | Br | O | nD 1.5396 (20.8° C.) |
| 34 | OCH(CH₃)COOC₂H₅ | CHF₂ | F | Cl | O | m.p. 67.0–67.2° C. |
| 35 | OCH(CH₃)COOC₃H₇-i | CH₃ | Cl | Cl | S | m.p. 87–90° C. |
| 36 | SCH(CH₃)COOCH₃ | CHF₂ | Cl | Cl | O | nD 1.5654 (19.8° C.) |
| 37 | SCH(CH₃)COOCH₃ | CHF₂ | F | Cl | O | nD 1.5494 (25.0° C.) |
| 38 | SCH(CH₃)COOC₂H₅ | CHF₂ | Cl | Cl | O | nD 1.5565 (28.0° C.) |
| 39 | SCH(CH₃)COOC₂H₅ | CHF₂ | F | Cl | O | nD 1.5328 (18.0° C.) |
| 40 | NHCH(CH₃)COOCH₃ | CH₃ | Cl | Cl | S | m.p. 144.2° C. |
| 41 | NHCH(CH₃)COOC₂H₅ | CH₃ | Cl | Cl | S | paste |
| 42 | NHCH(CH₃)COOC₂H₅ | CHF₂ | Cl | Cl | O | nD 1.5371 (23.4° C.) |
| 43 | NHCH(CH₃)COOC₂H₅ | CHF₂ | F | Cl | O | nD 1.5264 (26.6° C.) |
| 44 | COOCH₂COOCH₃ | CHF₂ | Cl | Cl | O | m.p. 74.4° C. |
| 45 | COOCH₂COOCH₃ | CHF₂ | F | Cl | O | nD 1.5350 (27.3° C.) |
| 46 | COOCH₂COSCH₃ | CHF₂ | Cl | Cl | O | |
| 47 | COOCH₂COSCH₃ | CHF₂ | F | Cl | O | |
| 48 | COOCH₂COOC₂H₅ | CHF₂ | Cl | Cl | O | m.p. 57.2° C. |
| 49 | COOCH₂COOC₂H₅ | CHF₂ | F | Cl | O | nD 1.5362 (23.4° C.) |
| 50 | COOCH₂COSC₂H₅ | CHF₂ | Cl | Cl | O | nD 1.5763 (20.7° C.) |
| 51 | COOCH₂COSC₂H₅ | CHF₂ | F | Cl | O | nD 1.5536 (27.3° C.) |
| 52 | COOCH₂COOC₃H₇-i | CHF₂ | Cl | Cl | O | nD 1.5289 (24.0° C.) |
| 53 | COOCH₂COOC₃H₇-i | CHF₂ | F | Cl | O | |
| 54 | COOCH₂COSC₃H₇-i | CHF₂ | Cl | Cl | O | nD 1.5684 (20.2° C.) |
| 55 | COOCH₂COSC₃H₇-i | CHF₂ | F | Cl | O | |
| 56 | COOCH₂COOCH₂CH=CH₂ | CHF₂ | Cl | Cl | O | m.p. 45.4° C. |
| 57 | COOCH₂COOCH₂CH=CH₂ | CHF₂ | F | Cl | O | |
| 58 | COOCH₂COOCH₂C≡CH | CHF₂ | Cl | Cl | O | m.p. 79.3° C. |
| 59 | COOCH₂COOCH₂C≡CH | CHF₂ | F | Cl | O | |
| 60 | COOCH(CH₃)COOCH₃ | CHF₂ | Cl | Cl | O | nD 1.5370 (25.7° C.) |
| 61 | COOCH(CH₃)COOCH₃ | CHF₂ | F | Cl | O | nD 1.5314 (23.0° C.) |
| 62 | COOCH(CH₃)COOC₂H₅ | CHF₂ | Cl | Cl | O | nD 1.5672 (26.0° C.) |
| 63 | COOCH(CH₃)COOC₂H₅ | CHF₂ | F | Cl | O | nD 1.5212 (14.1° C.) |
| 64 | COOCH₂C≡CH | CHF₂ | Cl | Cl | O | m.p. 78.5° C. |

TABLE 1-continued $$\text{(I)}$$

Structure: 4-chloro-2-X¹-phenyl group at pyrazole 3-position; pyrazole has X² at 4-position, R at 5-position (via chloro-substituted phenyl), N-R¹, and —(Y)n—R² at 5-position.

| | R | R² | X¹ | X² | (Y)n | Physical property |
|---|---|---|---|---|---|---|
| 65 | COOCH₃ | CHF₂ | Cl | Cl | O | m.p. 63.9° C. |
| 66 | COOCH₃ | CHF₂ | F | Cl | O | nD 1.5430 (17.0° C.) |
| 67 | COOC₂H₅ | CH₃ | Cl | Cl | O | nD 1.6029 (20.1° C.) |
| 68 | COOC₂H₅ | CHF₂ | Cl | Cl | O | nD 1.5446 (26.8° C.) |
| 69 | COOC₂H₅ | CHF₂ | F | Cl | O | nD 1.5320 (21.0° C.) |
| 70 | OCH₂CH=CH₂ | CHF₂ | Cl | Cl | NH | m.p. 80.6° C. |
| 71 | OCH₂C≡CH | CHF₂ | Cl | Cl | NH | m.p. 118.9° C. |
| 72 | OCH₂COOCH₃ | i-C₃H₇ | Cl | Cl | — | paste |
| 73 | OCH₂CH=CH₂ | i-C₃H₇ | Cl | Cl | — | paste |
| 74 | OCH₂C≡CH | i-C₃H₇ | Cl | Cl | — | paste |
| 75 | SCH₂COOCH₃ | t-C₄H₉ | Cl | Cl | — | paste |
| 76 | OCH₂CH=CH₂ | CH₂Br | Cl | Cl | — | paste |

R¹ = CH₃

The composition for regulating plant growth of the present invention can be applied in the form of an emulsifiable concentrate, wettable powder, aqueous suspension or the like prepared according to an ordinary manner for preparation of agrochemicals by blending one or more active ingredients selected from 3-substituted phenylpyrazole derivatives of the general formula (I) with one or more materials selected from the group consisting of suitable solid carriers and liquid carriers, and optionally adjuvants, etc., in a proportion properly chosen in the range of 0.1 to 90 parts by weight per 100 parts by weight of the composition.

The composition for regulating plant growth of the present invention can be used as a desiccant or defoliant for, for example, root vegetables (e.g. potato), fiber crops (e.g. cotton), oil crops (e.g. soybean and sunflower) and cereals (e.g. rice), but these examples of use are not intended in any way to limit the scope of the present invention.

The composition for regulating plant growth of the present invention may contain other active ingredients for regulating plant growth for the purpose of, for example, reducing the dosage. Examples of the other active ingredients are given below.

When used as a desiccant, the composition may be incorporated with, for example, quaternary ammonium salts such as 1,1'-dimethyl-4,4'-bipyridinium (Common name: Paraquat), 9,10-dihydro-8a,10a-diazoniaphenanthrene (Common name: Diquat), etc.; organophosphorus compounds such as N-(phosphoromethyl)glycine (Common name: Glyphosate), N-(phosphoromethyl)glycine trimethylsulfonium salt (Common name: Glyphosate Trimecium), 2-chloroethylphosphonic acid (Common name: Ethephon), etc.; inorganic compounds such as sodium chlorate (NaClO₃), magnesium chlorate (Mg(ClO₃) 6H₂O), ammonia, lime nitrogen (Ca(NCN)/CaCN₂), etc.; aliphatic compounds such as sodium monochloroacetate (Common name: Chloroacetic Acid), sodium trichloroacetate (Common name: TCA), hexachloroacetone, etc.; phenolic compounds such as 2-sec-butyl-4,6-dinitrophenol (Common name: Dinoseb), pentachlorophenol (Common name: PCP) and its salts, etc.; triazine type compounds such as N ethyl-N isopropyl-6-methylthio-1,3,5-triazine-2,4-diamine (Common name: Ametryn), etc.; arsenic acid type compounds such as arsenic acid, etc.; machine oil; and 7-oxabicyclo[2,2,1]heptane-2,3-dicarboxylic acid (Common name: Endothal) and its amine salt, sodium salt or potassium salt.

When used as a defoliant, the composition may be incorporated with, for example, organophosphorus compounds such as Ethephon, S,S,S-tributylphosphorotrithioate, S,S,S-tributylphosphorotrithioite, etc.; inornic compounds such as lime nitrogen, sodium chlorate, ammonium nitrate, ammonium thiocyanate, zinc chloride, sodium hypochlorite, etc.; arsenic acid type compounds such as methylarsonic acid and its salts, etc.; aliphatic compounds such as Chloroacetic Acid, etc.; Endothal; 1H-1,2,4-triazol-3-ylamine (Common name: Amitrole); and thioureas. The above-exemplified compounds are not intended in any way to limit the scope of the present invention.

Typical examples, test examples and the like of the present invention are described below as embodiments of the present invention but they should not be construed as limiting the scope of the invention.

In the examples, parts are all by weight.

Example 1

| | |
|---|---|
| Compound No. 19 | 0.4 part |
| Solvesso 200 | 57.6 parts |
| Polyoxyethylene lauryl ether (HLB 10.0) | 40.0 parts |
| SP-3005X | 2.0 parts |

An emulsifiable concentrate was prepared by mixing uniformly the above ingredients to effect dissolution.

Examples 2 to 7

Compositions for regulating plant growth were prepared according to each recipe shown in Table 2, in the same manner as in Example 1.

TABLE 2

| Composition | 2 | 3 | 4 | 5 | 6 | 7 |
|---|---|---|---|---|---|---|
| Compound No. 19 | 0.2 | 0.4 | 0.4 | 0.4 | 1.0 | 2.5 |
| Solvesso 200 (mfd. by Exxon Chemical Co., Ltd.) | 76.8 | 57.6 | 56.6 | 55.6 | 76.0 | 77.5 |
| POE Lauryl ether (HLB 14.0) | 20.0 | | | | | |
| POE Styrylphenyl ether (HLB 15.5) | | 40.0 | | | | |
| POE (10 mols) Nonylphenyl ether | | | 40.0 | | | |
| POE (12 mols) Nonylphenyl ether | | | | 40.0 | | |
| POE Fatty acid ester (HLB 9.5) | | | | | 20.0 | |
| N-Methyl-2-pyrrolidone | | | | | | 10.0 |
| SP-3005X (mfd. by TOHO KAGAKU K. K.) | 3.0 | 2.0 | 3.0 | 4.0 | 3.0 | 10.0 |
| | 100.0 | 100.0 | 100.0 | 100.0 | 100.0 | 100.0 |

Test Example 1

Desiccant Effect on Potato

Potate tubers (*Solanum tuberosum*, cultivar: May Queen) were trans-planted at a 0.4 m interval in a row of 1.0 m width. When the growth stage reached the beginning of yellowing, the stems and leaves were uniformly treated with a predetermined dosage of each of the composition for regulating plant growth of the present invention described in Example 1 and reference agents in a spray volume of 1000 liters/ha.

Seven days and 14 days after the treatment, the desiccant effect on the stems and leaves was visually judged according to the criterion shown below.

In addition, 14 days after the treatment, the tubers were dug out and the degree of browning of the vascular bundle was judged in terms of an index according to the criterion shown below.

Criterion for judging the desiccant effect:

| Efficacy | Withered area of stems and leaves (%) |
|---|---|
| 1 | 0–49 |
| 2 | 50–69 |
| 3 | 70–89 |
| 4 | 90–99 |
| 5 | 100 |

Criterion (indexes) for judging the browning of vascular bundle:

0: No browning of vascular bundle
1: Slight browning of vascular bundle near the base
2: Browning of less than ⅓ of vascular bundle
3: Browning of ⅓ to ⅔ of vascular bundle
4: Browning of the whole vascular bundle Table 3 shows the results of investigating the desiccant effect and Table 4 the results of judging the browning of the vascular bundle.

TABLE 3

| | | | Dessicant effect | | | |
|---|---|---|---|---|---|---|
| | | | Leaves | | Stems | |
| | Test agent | Dosage (gAI/ha) | After 7 days | After 14 days | After 7 days | After 14 days |
| Invention | Example 1 | 10 | 4 | 5 | 3 | 4 |
| | | 20 | 5 | 5 | 4 | 5 |
| | | 40 | 5 | 5 | 4 | 5 |
| Reference | Diquat | 900 | 5 | 5 | 3 | 4 |
| | Lime nitrogen | 15 kg/10a | 4 | 5 | 1 | 4 |

Note: As lime nitrogen, a commercial one containing 50% calcium cyanamide was used. AI denotes an active ingredient.

TABLE 4

| | | Browing of vascular bundle | | | | |
|---|---|---|---|---|---|---|
| | | Percentage of browning of vascular bundle (%) Index of browning of vascular bundle | | | | |
| | Test agent | Dosage (gAI/ha) | 0 | 1 | 2 | 3 | 4 |
| Invention | Example 1 | 10 | 100 | 0 | 0 | 0 | 0 |
| | | 20 | 75 | 25 | 0 | 0 | 0 |
| | | 40 | 70 | 30 | 0 | 0 | 0 |
| Reference | Diquat | 900 | 0 | 56 | 44 | 0 | 0 |
| | Lime nitrogen | 15 kg/10a | 75 | 25 | 0 | 0 | 0 |

Test Example 2

Seeds of cotton (*Gossypium hirsutum*, cultivar: Acala) were sown at 0.4-m intervals and grown. At the time of the dehiscence of cotton boll, the leaves were uniformly treated with a predetermined dosage of each of the composition for regulating plant growth of the present invention described in Example 1 and reference agents in a volume rate of 250 liters/ha.

Five, 10, 15 and 20 days after the treatment, the desiccant effect on the leaves was visually judged in the range of 0 (the same result as in the case of no treatment) to 100 (complete withering). As to the defoliating effect, the defoliation rate was calculated 15 and 20 days after the treatment by the equation shown below.

In addition, 25 days after the treatment, the phytotoxicity to lint (harvest) was investigated and then judged according to the criterion shown below.

Defoliation rate:

$$\text{Defoliation rate } (\%) = \frac{\text{Number of fallen leaves}}{\text{Total number of examined leaves}} \times 100$$

Criterion for judging the phytotoxicity to lint:

+: phytotoxicity was shown
−: no phytotoxicity was shown

Table 5 shows the results of investigating the leave-withering effect and Table 6 the results of investigating the defoliating effect and the results of investigating the phytotoxicity to lint.

TABLE 5

| Test agent | | Dosage (gAI/ha) | desiccant effect on leaves | | | |
|---|---|---|---|---|---|---|
| | | | After 5 days | After 10 days | After 15 days | After 25 days |
| Invention | Example 1 | 5 | 80 | 90 | 93 | 100 |
| | | 10 | 80 | 90 | 95 | 100 |
| | | 20 | 90 | 95 | 97 | 100 |
| Reference | Diquat | 1000 | 90 | 95 | 98 | 100 |

TABLE 6

| Test agent | | Dosage (gAI/ha) | defoliating effect on leaves | | Phytotoxicity (lint) |
|---|---|---|---|---|---|
| | | | After 15 days | After 25 days | After 25 days |
| Invention | Example 1 | 5 | 30 | 70 | — |
| | | 10 | 30 | 70 | — |
| | | 20 | 40 | 75 | — |
| Reference | Diquat | 1000 | 8 | 10 | — |

What is claimed is:

1. A method of defoliating plants which comprises applying a composition, comprising as an active ingredient, at least one 3-substituted pyrazole derivative in a defoliating effective amount, in terms of the active ingredient, per hectare, to plants requiring defoliation, said 3-substituted pyrazole derivative represented by the general formula (I):

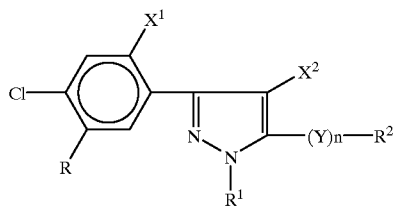

(I)

wherein R is

—Y$^1$R$^3$ (wherein R$^3$ is a (C$_{1-6}$)alkyl group, a halo(C$_{1-6}$)alkyl group, a (C$_{2-6}$)alkenyl group or a (C$_{2-6}$)alkynyl group, and Y$^1$ is —O— or —S—,

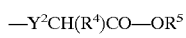

—Y$^2$CH(R$^4$)CO—OR$^5$ (wherein R$^4$ is a hydrogen atom or a (C$_{1-6}$)alkyl group, R$^5$ is a hydrogen atom, a (C$_{1-6}$)alkyl group, a halo(C$_{1-6}$)alkyl group, a (C$_{2-6}$)alkenyl group or a (C$_{2-6}$)alkynyl group, and Y$^2$ is —O—, —S— or —NH—),

—COOCH(R$^4$)CO—Y$^1$ R$^5$ (wherein R$^4$, R$^5$ and Y$^1$ are as defined above), or —COOR$^6$ (wherein R$^6$ is a (C$_{1-6}$)alkyl group, a halo(C$_{1-6}$)alkyl group, a (C$_{2-6}$)alkenyl group or a (C$_{2-6}$)alkynyl group,
R$^1$ is a (C$_{1-6}$)alkyl group, R$^2$ is a hydrogen atom, (C$_{1-6}$)alkyl group or a halo (C$_{1-6}$)alkyl group, X$^1$ and X$^2$, which may be the same or different, are halogen atoms,
Y is —O—, —S—, —SO—, —SO$_2$—, or —NH—, and n is an integer of 0 or 1.

2. A method of desiccating plants which comprises applying a composition, comprising as an active ingredient, at least one 3-substituted pyrazole derivative in a desiccating effective amount, in terms of the active ingredient, per hectare, to plants requiring desiccation, said 3-substituted pyrazole derivative represented by the general formula (I):

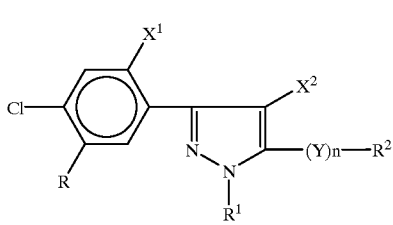

(I)

wherein R is

—Y$^1$R$^3$ (wherein R$^3$ is a (C$_{1-6}$)alkyl group, a halo(C$_{1-6}$)alkyl group, a (C$_{2-6}$)alkenyl group or a (C$_{2-6}$)alkynyl group, and Y$^1$ is —O— or —S—,

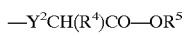

—Y$^2$CH(R$^4$)CO—OR$^5$ (wherein R$^4$ is a hydrogen atom or a (C$_{1-6}$)alkyl group, R$^5$ is a hydrogen atom, a (C$_{1-6}$)alkyl group, a halo(C$_{1-6}$)alkyl group, a (C$_{2-6}$)alkenyl group or a (C$_{2-6}$)alkynyl group, and Y$^2$ is —O—, —S— or —NH—),

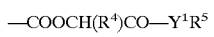

—COOCH(R$^4$)CO—Y$^1$R$^5$ (wherein R$^4$, R$^5$ and Y$^1$ are as defined above), or —COOR$^6$ (wherein R$^6$ is a (C$_{1-6}$)alkyl group, a halo(C$_{1-6}$)alkyl group, a (C$_{2-6}$)alkenyl group or a (C$_{2-6}$)alkynyl group,
R$^1$ is a (C$_{1-6}$)alkyl group, R$^2$ is a hydrogen atom, (C$_{1-6}$)alkyl group or a halo (C$_{1-6}$)alkyl group, X$^1$ and X$^2$, which may be the same or different, are halogen atoms,
Y is —O—, —S—, —SO—, —SO$_2$—, or —NH—, and n is an integer of 0 or 1.

3. A method of defoliating plants which comprises applying a composition, comprising as an active ingredient, at least one 3-substituted pyrazole derivative in a defoliating effective amount, in terms of the active ingredient, per hectare, to plants requiring defoliation, said 3-substituted pyrazole derivative represented by the general formula (I):

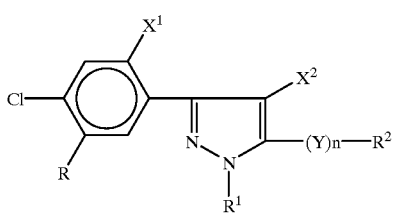

(I)

wherein R is

—Y$^1$R$^3$ (wherein, R$^3$ is a (C$_{1-6}$)alkyl group, a halo(C$_{1-6}$)alkyl group, a (C$_{2-6}$)alkenyl group or a (C$_{2-6}$)alkynyl group, and Y$^1$ is —O— or —S—,

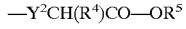

—Y$^2$CH(R$^4$)CO—OR$^5$ (wherein $R^4$ is a hydrogen atom or a $(C_{1-6})$alkyl group, $R^5$ is a hydrogen atom, a $(C_{1-6})$alkyl group, a halo$(C_{1-6})$alkyl group, a $(C_{2-6})$alkenyl group or a $(C_{2-6})$alkynyl group, and $Y^2$ is —O—, —S— or —NH—),

—COOCH($R^4$)CO—$Y^2R^5$ (wherein $R^4$, $R^5$ and $Y^2$ are as defined above), or —COOR$^6$ (wherein $R^6$ is a $(C_{1-6})$alkyl group, a halo$(C_{1-6})$alkyl group, a $(C_{2-6})$alkenyl group or a $(C_{2-6})$alkynyl group, $R^1$ is a $(C_{1-6})$alkyl group, $R^2$ is a hydrogen atom, $(C_{1-6})$alkyl group or a halo $(C_{1-6})$alkyl group, $X^1$ and $X^2$, which may be the same or different, are halogen atoms, Y is —O—, —S—, —SO—, —SO$_2$—, or —NH—, and n is an integer of 0 or 1, and wherein said 3-substituted pyrazole derivative is incorporated with one of more of: a quaternary ammonium salt; organophosphorus compounds; inorganic compounds selected from the group consisting of sodium chlorate, magnesium chlorate, ammonia, and lime nitrogen; aliphatic compounds; phenolic compounds and corresponding salts; triazine compounds; arsenic acid compounds; machine oil; and 7-oxabicyclo(2,2,1)heptane-2,3-dicarboxylic acid and its amine salt, sodium salt or potassium salt.

4. A method of desiccating plants which comprises applying a composition, comprising as an active ingredient, at least one 3-substituted pyrazole derivative in a desiccating effective amount, in terms of the active ingredient, per hectare, to plants requiring desiccation, said 3-substituted pyrazole derivative represented by the general formula (I):

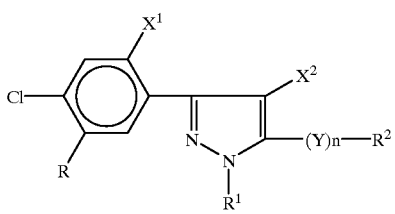

wherein R is

—$Y^1R^3$ (wherein $R^3$ is a $(C_{1-6})$alkyl group, a halo$(C_{1-6})$alkyl group, a $(C_{2-6})$alkenyl group or a $(C_{2-6})$alkynyl group, and $Y^1$ is —O— or —S—,

—$Y^2$CH($R^4$)CO—OR$^5$ (wherein $R^4$ is a hydrogen atom or a $(C_{1-6})$alkyl group, $R^5$ is a hydrogen atom, a $(C_{1-6})$alkyl group, a halo$(C_{1-6})$alkyl group, a $(C_{2-6})$alkenyl group or a $(C_{2-6})$alkynyl group, and $Y^2$ is —O—, —S— or —NH—),

—COOCH($R^4$)CO—$Y^1R^5$ (wherein $R^4$, $R^5$ and $Y^1$ are as defined above), or —COOR$^6$ (wherein $R^6$ is a $(C_{1-6})$alkyl group, a halo$(C_{1-6})$alkyl group, a $(C_{2-6})$alkenyl group or a $(C_{2-6})$alkynyl group, $R^1$ is a $(C_{1-6})$alkyl group, $R^2$ is a hydrogen atom, $(C_{1-6})$alkyl group or a halo $(C_{1-6})$alkyl group, $X^1$ and $X^2$, which may be the same or different, are halogen atoms, Y is —O—, —S—, —SO—, —SO$_2$—, or —NH—, and n is an integer of 0 or 1, and wherein said 3-substituted pyrazole derivative is incorporated with one of more of: an organophosphorus compounds; inorganic compounds selected from the group consisting of lime nitrogen, sodium chlorate, ammonium nitrate, ammonium thiocyanate, zinc chloride and sodium hypochlorite; arsenic acid compounds and corresponding salts; aliphatic compounds; and thioureas.

5. A method for regulating the growth of plants according to claim 3, or claim 4 wherein the 3-substituted pyrazole derivative represented by the general formula (I) is ethyl 2-chloro-5-(4-chloro-5-difluoromethoxy-1-methyl-1H-pyrazol-3-yl)-4-fluorophenoxyacetate.

6. A method for regulating the growth of plants according to claim 3 or claim 4, wherein the plants are selected from the group consisting of root vegetables, fiber crops, oil crops and cereals.

7. A method for regulating the growth of plants according to claim 6, wherein the root vegetable is potato.

8. A method for regulating the growth of plants according to claim 6, wherein the fiber crop is cotton.

9. A method for regulating the growth of plants according to claim 6, wherein the oil crop is selected from the group consisting of soybean and sunflower.

10. A method for regulating the growth of plants according to claim 6, wherein the cereal is rice.

* * * * *